United States Patent
Hashimoto et al.

(10) Patent No.: US 11,304,888 B2
(45) Date of Patent: Apr. 19, 2022

(54) ORAL CARE COMPOSITION

(71) Applicant: SUNSTAR AMERICAS, INC., Schaumburg, IL (US)

(72) Inventors: Kana Hashimoto, Mount Prospect, IL (US); Toru Saito, Buffalo Grove, IL (US)

(73) Assignee: SUNSTAR AMERICAS, INC., Schaumburg, IL (US)

(*) Notice: Subject to any disclaimer, the term of this patent is extended or adjusted under 35 U.S.C. 154(b) by 0 days.

(21) Appl. No.: 16/704,911

(22) Filed: Dec. 5, 2019

(65) Prior Publication Data

US 2020/0337975 A1 Oct. 29, 2020

Related U.S. Application Data

(60) Provisional application No. 62/840,229, filed on Apr. 29, 2019.

(51) Int. Cl.
| | | |
|---|---|---|
| *A61K 8/64* | (2006.01) | |
| *A61K 8/02* | (2006.01) | |
| *A61Q 11/00* | (2006.01) | |
| *A61K 8/36* | (2006.01) | |

(52) U.S. Cl.
CPC ............... *A61K 8/64* (2013.01); *A61K 8/02* (2013.01); *A61K 8/36* (2013.01); *A61Q 11/00* (2013.01); *A61K 2800/59* (2013.01); *A61K 2800/92* (2013.01)

(58) Field of Classification Search
CPC ... A61K 8/19; A61K 8/36; A61K 8/64; A61K 8/02; A61K 2800/59; A61K 2800/92; A61Q 11/00
See application file for complete search history.

(56) References Cited

U.S. PATENT DOCUMENTS

| | | |
|---|---|---|
| 3,935,304 A | 1/1976 | Januszewski et al. |
| 3,935,305 A | 1/1976 | Delaney et al. |
| 3,937,321 A | 2/1976 | Delaney et al. |
| 3,943,240 A | 3/1976 | Delaney et al. |
| 4,160,022 A | 7/1979 | Delaney et al. |
| 4,575,457 A | 3/1986 | Mazarin |
| 4,603,045 A | 7/1986 | Smigel |
| 4,623,536 A | 11/1986 | Winston et al. |
| 4,690,776 A | 9/1987 | Smigel |
| 4,721,614 A | 1/1988 | Winston et al. |
| 4,812,306 A | 3/1989 | Cocherell et al. |
| 4,891,211 A | 1/1990 | Winston |
| 5,004,596 A | 4/1991 | Cocherell et al. |
| 5,041,280 A | 8/1991 | Smigel |
| 5,135,910 A | 8/1992 | Blackburn et al. |
| 5,217,950 A | 6/1993 | Blackburn et al. |
| 5,260,271 A | 11/1993 | Blackburn et al. |
| 5,304,540 A | 4/1994 | Blackburn et al. |
| 5,334,582 A | 8/1994 | Blackburn et al. |
| 5,376,360 A | 12/1994 | Domke et al. |
| 5,424,060 A | 6/1995 | Hauschild |
| 5,670,138 A | 9/1997 | Venema et al. |
| 5,686,064 A | 11/1997 | Gaffar et al. |
| 5,763,395 A | 6/1998 | Blackburn et al. |
| 5,833,958 A | 11/1998 | Doel et al. |
| 5,840,281 A | 11/1998 | Gaffar et al. |
| 6,207,411 B1 | 3/2001 | Ross et al. |
| 7,387,774 B2 | 6/2008 | Faller et al. |
| 8,501,161 B2 | 8/2013 | Prencipe et al. |
| 8,652,495 B2 | 2/2014 | Porter et al. |
| 8,900,558 B2 | 12/2014 | Joziak et al. |
| 9,320,699 B2 | 4/2016 | Porter et al. |
| 9,358,185 B2 | 6/2016 | Haeberlein et al. |
| 2004/0018155 A1 | 1/2004 | Hoagland |
| 2005/0158252 A1 | 7/2005 | Romanowski et al. |
| 2007/0053849 A1 | 3/2007 | Doyle et al. |
| 2008/0241117 A1 | 10/2008 | Gaffar et al. |
| 2008/0267891 A1 | 10/2008 | Zaidel et al. |
| 2009/0053267 A1 | 2/2009 | DePierro et al. |
| 2009/0186090 A1 | 7/2009 | Zaidel et al. |
| 2009/0269288 A1 | 10/2009 | Lavrova |
| 2012/0020899 A1 | 1/2012 | Zaidel et al. |
| 2012/0301852 A1 | 11/2012 | Xu et al. |
| 2015/0125814 A1 | 5/2015 | Haeberlein et al. |
| 2016/0193124 A1 | 7/2016 | Porter et al. |
| 2018/0116924 A1 | 5/2018 | Prencipe et al. |

FOREIGN PATENT DOCUMENTS

| | | |
|---|---|---|
| BG | 65539 B1 | 11/2008 |
| CA | 992867 A | 7/1976 |
| CA | 2116225 C | 6/1999 |
| CA | 2916864 A1 | 5/2014 |
| CN | 1899261 B | 5/2010 |
| CN | 101647768 B | 6/2011 |
| CN | 102525856 A | 7/2012 |

(Continued)

OTHER PUBLICATIONS

International Search Report and Written Opinion for Application No. PCT/US2020/029363 dated Jul. 22, 2020 (15 pages).
Cunha et al., "Potential of two delivery systems for nisin topical application to dental plaque biofilms in dogs," BMC Veterinary Research, 2018, vol. 14, Article 375, pp. 1-10.
Belizário et al., "Human Microbiomes and their Roles in Dysbiosis, Common Diseases, and Novel Therapeutic Approaches," Frontiers in Microbiology, 2015, vol. 6, Article 1050, pp. 1-16.
Chow et al., "Host-Bacterial Symbiosis in Health and Disease," Advances in Immunology, 2010, vol. 107, pp. 243-274.
Clemente et al., "The Impact of the Gut Microbiota on Human Health: An Integrative View," Cell, 2012, vol. 148, pp. 1258-1270.

(Continued)

*Primary Examiner* — Lezah Roberts
(74) *Attorney, Agent, or Firm* — Michael Best & Friedrich LLP

(57) ABSTRACT

An oral care composition including a base formulation, sodium bicarbonate, and nisin, wherein the oral care composition removes biofilm from a tooth surface more effectively than the base formulation with the sodium bicarbonate or the nisin alone.

17 Claims, 7 Drawing Sheets

(56) References Cited

FOREIGN PATENT DOCUMENTS

| | | |
|---|---|---|
| CN | 102871902 A | 1/2013 |
| CN | 102871903 A | 1/2013 |
| CN | 103040659 A | 4/2013 |
| CN | 103156788 A | 6/2013 |
| CN | 103479543 A | 1/2014 |
| CN | 103610610 A | 3/2014 |
| CN | 103655306 A | 3/2014 |
| CN | 103893038 A | 7/2014 |
| CN | 104173209 A | 12/2014 |
| CN | 104306232 A | 1/2015 |
| CN | 104306237 A | 1/2015 |
| CN | 104546535 A | 4/2015 |
| CN | 104856903 A | 8/2015 |
| CN | 105326656 A | 2/2016 |
| CN | 105326708 A | 2/2016 |
| CN | 105708783 A | 6/2016 |
| CN | 105997719 A | 10/2016 |
| CN | 106176378 A | 12/2016 |
| CN | 106214559 A | 12/2016 |
| CN | 104224627 B | 1/2017 |
| CN | 106265267 A | 1/2017 |
| CN | 106420552 A | 2/2017 |
| CN | 106491406 A | 3/2017 |
| CN | 106619399 A | 5/2017 |
| CN | 106619424 A | 5/2017 |
| CN | 106727152 A | 5/2017 |
| CN | 106806304 A | 6/2017 |
| CN | 106924170 A | 7/2017 |
| CN | 106983681 A | 7/2017 |
| CN | 107007539 A | 8/2017 |
| CN | 107028796 A | 8/2017 |
| CN | 107049810 A | 8/2017 |
| CN | 107049876 A | 8/2017 |
| CN | 107080731 A | 8/2017 |
| CN | 107095838 A | 8/2017 |
| CN | 107126387 A | 9/2017 |
| CN | 107137297 A | 9/2017 |
| CN | 107280985 A | 10/2017 |
| CN | 107308077 A | 11/2017 |
| CN | 106619193 B | 1/2018 |
| CN | 107550766 A | 1/2018 |
| CN | 107982073 A | 5/2018 |
| CN | 107982185 A | 5/2018 |
| CN | 108096093 A | 6/2018 |
| CN | 108261370 A | 7/2018 |
| CN | 108618977 A | 10/2018 |
| CN | 108685716 A | 10/2018 |
| CN | 110522675 A | 12/2019 |
| EA | 000508 B1 | 10/1999 |
| GB | 551369 A | 2/1943 |
| GB | 1209319 A | 10/1970 |
| GB | 1413642 A | 11/1975 |
| GB | 1413643 A | 11/1975 |
| GB | 1498537 A | 1/1978 |
| JP | H02250816 A | 10/1990 |
| JP | 2561829 B2 | 12/1996 |
| JP | H10167939 A | 6/1998 |
| JP | H11279079 A | 10/1999 |
| JP | 3195150 B2 | 8/2001 |
| JP | 3241946 B2 | 12/2001 |
| JP | 3667472 B2 | 7/2005 |
| JP | 2011001352 A | 1/2011 |
| KR | 20000038940 A | 7/2000 |
| KR | 100321821 B1 | 1/2002 |
| KR | 100446855 B1 | 9/2004 |
| KR | 101544896 B1 | 8/2015 |
| MD | 4453 C1 | 7/2017 |
| NZ | 520393 A | 4/2004 |
| RO | 121587 B1 | 12/2007 |
| RO | 126742 B1 | 6/2014 |
| WO | 8912399 A1 | 12/1989 |
| WO | 9412150 A1 | 6/1994 |
| WO | 9506455 A1 | 3/1995 |
| WO | 9637181 A1 | 11/1996 |
| WO | 9710801 A2 | 3/1997 |
| WO | 2005037240 A1 | 4/2005 |
| WO | 2017014682 A2 | 1/2017 |
| WO | 2017069227 A1 | 4/2017 |

OTHER PUBLICATIONS

Do et al., "Oral Biofilms: Molecular Analysis, Challenges, and Future Prospects in Dental Diagnostics," Clinical, Cosmetic and Investigational Dentistry, 2013, vol. 5, pp. 11-19.

Filoche et al., "Oral Biofilms: Emerging Concepts in Microbial Ecology," Journal of Dental Research, 2010, vol. 89, Issue 1, pp. 8-18.

Ghassemi et al., "A Four-Week Clinical Study to Evaluate and Compare the Effectiveness of a Baking Soda Dentifrice and an Antimicrobial Dentifrice in Reducing Plaque," The Journal of Clinical Dentistry, 2008, vol. 19, Issue 4, pp. 120-126.

Jiang et al., "Pyrosequencing Analysis of Oral Microbiota Shifting in Various Caries States in Childhood," Microbial Ecology, 2014, vol. 67, pp. 962-969.

Marsh, "In Sickness and in Health—What Does the Oral Microbiome Mean to US? An Ecological Perspective," Advances in Dental Research, 2018, vol. 29, Issue 1, pp. 60-65.

Pérez-Chaparro et al., "Newly Identified Pathogens Associated with Periodontitis: A Systematic Review," Journal of Dental Research, 2014, vol. 93, Issue 9, pp. 846-858.

Relman, "The Human Microbiome: Ecosystem Resilience and Health," Nutrition Reviews, 2012, vol. 70, pp. S2-S9.

Sartor et al., "Intestinal Microbes in Inflammatory Bowel Diseases," The American Journal of Gastroenteroloy Supplements, 2012, vol. 1, Issue 1, pp. 15-21.

Shin et al., "Antimicrobial Nisin Acts Agains Saliva Derived Multi-Species Biofilms without Cytotoxicity to Human Oral Cells," Frontiers in Microbiology, 2015, vol. 6, Article 617, pp. 1-14.

Shin et al., "Biomedical Applications of Nisin," Journal of Applied Microbiology, 2015, pp. 1449-1465.

Thong et al., "Enhancement of Plaque Removal by Baking Soda Toothpastes from Less Accessible Areas in the Dentition," The Journal of Clinical Dentistry, 2011, vol. 22, Issue 5, pp. 171-178.

ORAL CARE COMPOSITION

CROSS-REFERENCE TO RELATED APPLICATIONS

This application claims priority to U.S. Provisional Patent Application No. 62/840,229, filed on Apr. 29, 2019, the entire contents of which is incorporated by reference herein.

FIELD OF DISCLOSURE

The present invention relates to an oral care composition for at least toothpaste, mouthwash, gel, chewing gum, and lozenges.

SUMMARY

One embodiment discloses an oral care composition that aids in cleaning teeth including greater than 0.0% by weight sodium bicarbonate and greater than 0.0% by weight of nisin to more effectively remove biofilm from a tooth surface than either sodium bicarbonate or nisin alone.

Another embodiment discloses a method of treating teeth including applying an oral care composition to a tooth surface. The composition includes greater than 0.0% by weight sodium bicarbonate and greater than 0.0% by weight of nisin to more effectively remove biofilm from a tooth surface than either sodium bicarbonate or nisin alone.

Another embodiment discloses an oral care composition that aids in cleaning teeth, the oral care composition including at least 15% by weight sodium bicarbonate and at least 0.000375% by weight of nisin, wherein a ratio of sodium bicarbonate to nisin is at least 500 to 1 and does not exceed 200,000 to 1.

Another embodiment discloses a method of treating teeth including applying an oral care composition to a tooth surface. The composition including at least 15% by weight sodium bicarbonate and at least 0.000375% by weight of nisin, wherein a ratio of sodium bicarbonate to nisin is at least 500 to 1 and does not exceed 200,000 to 1.

An oral care composition including a base formulation, sodium bicarbonate, and nisin, wherein the oral care composition removes biofilm from a tooth surface more effectively than the base formulation with the sodium bicarbonate or the nisin alone.

Other aspects of the invention will become apparent by consideration of the detailed description and accompanying figures.

DETAILED DESCRIPTION

Figure 1:
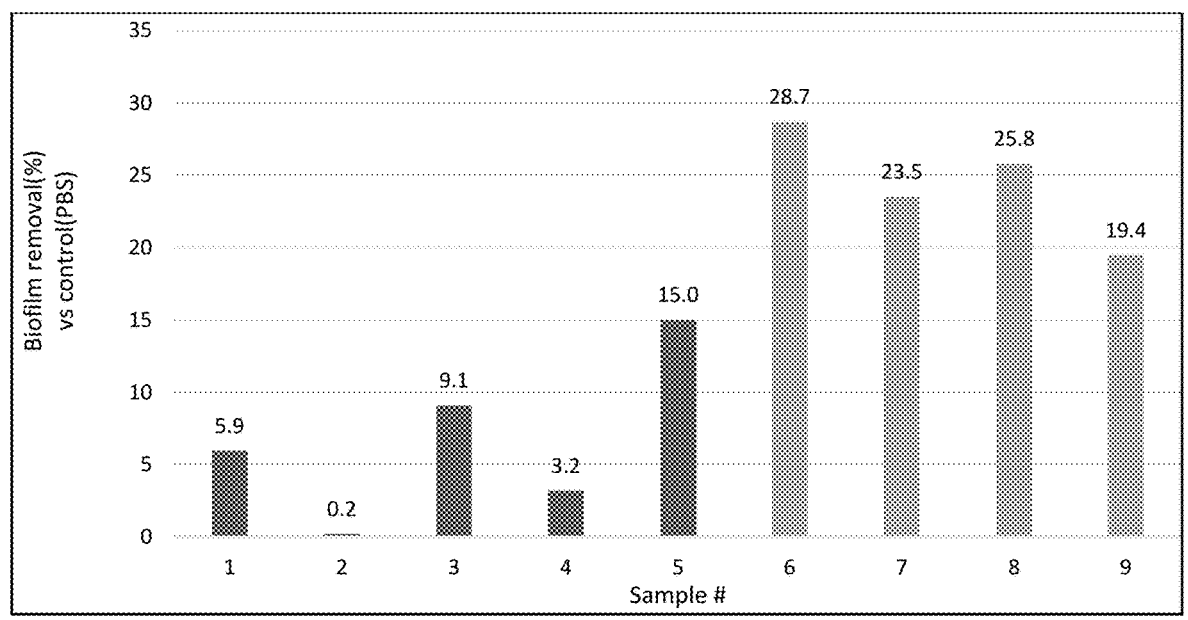
FIG. 1 graphically shows the results of Experiment 1.
Figure 2:
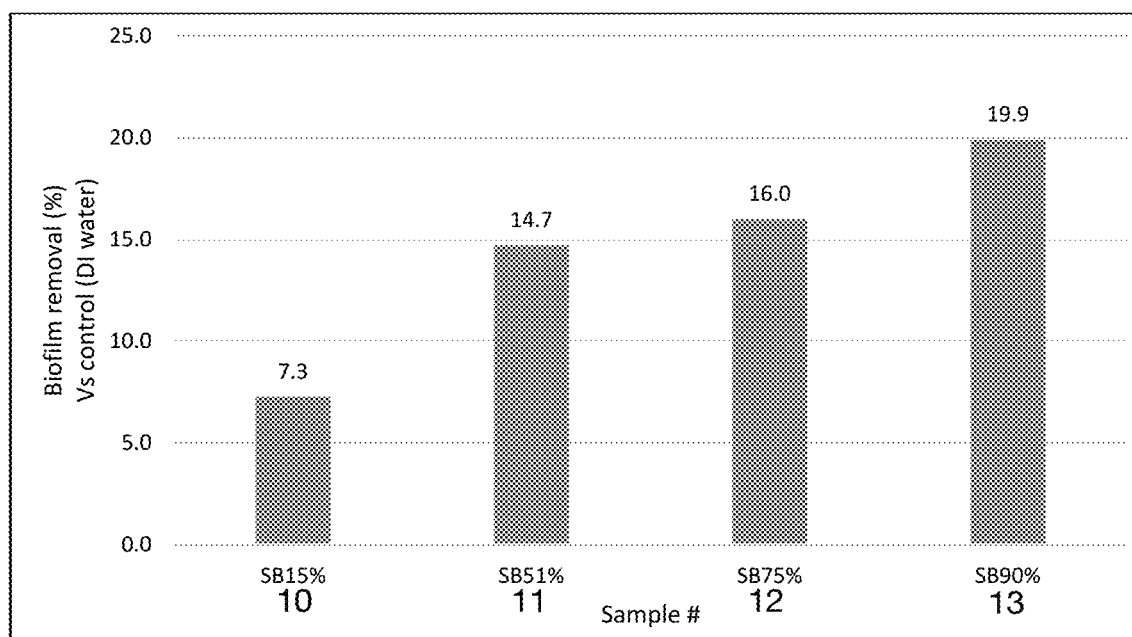
FIG. 2 graphically shows the results of Experiment 2 in which sample solution numbers 10-13 include 0.0% by weight nisin and varying concentrations of sodium bicarbonate.
Figure 3:
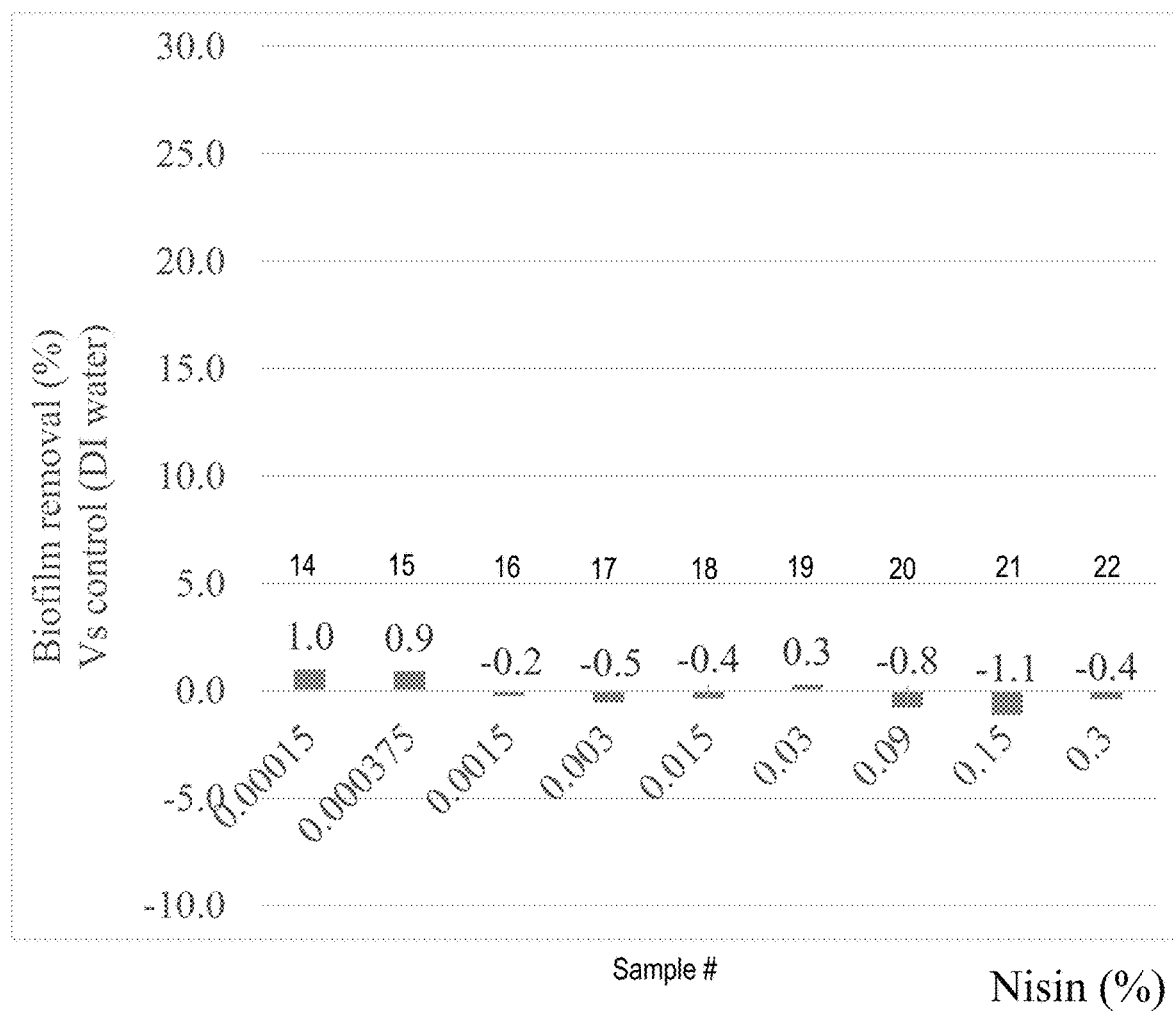
FIG. 3 graphically shows the results of Experiment 2 in which sample solution numbers 14-22 include varying concentrations of nisin and 0.0% by weight sodium bicarbonate.
Figure 4:
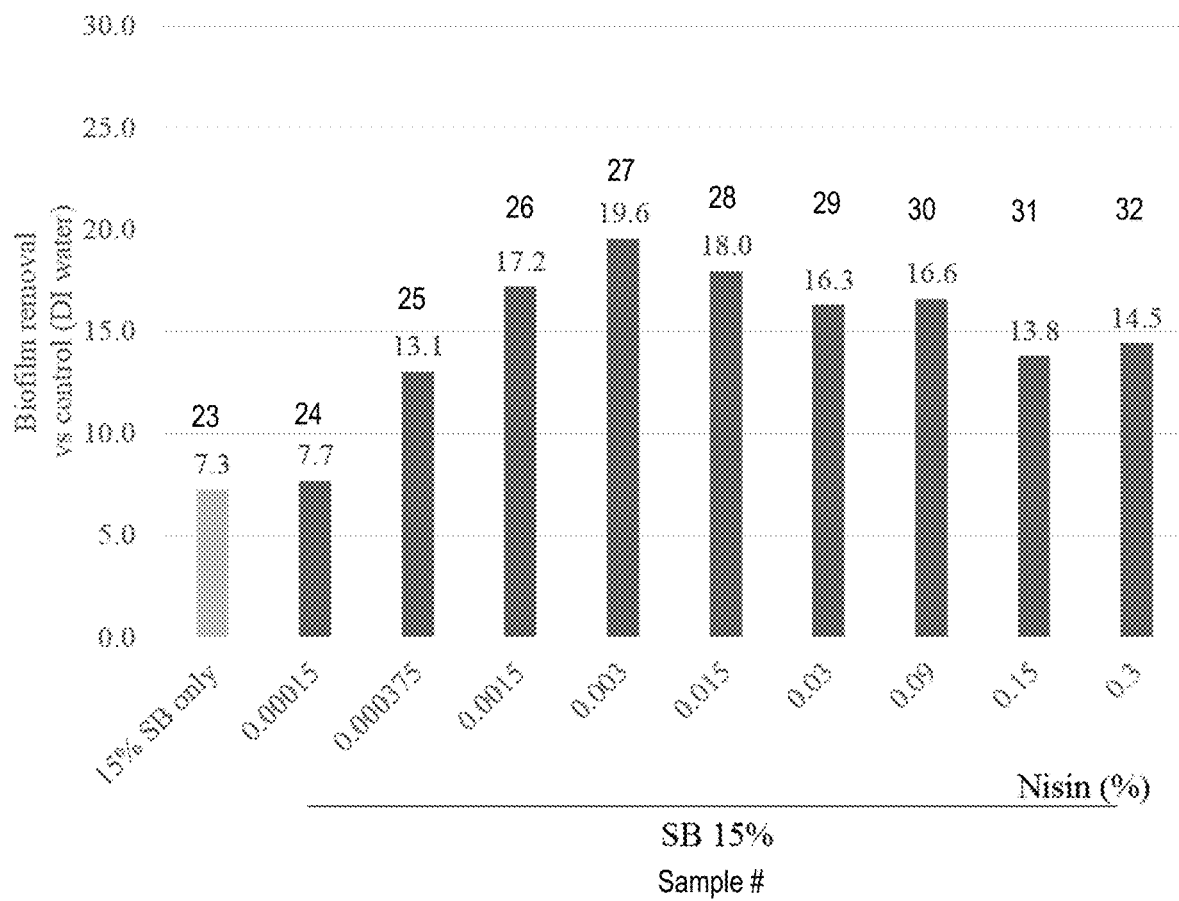
FIG. 4 graphically shows the results of Experiment 2 in which sample solution numbers 23-32 include varying concentrations of nisin and 15.0% by weight sodium bicarbonate.
Figure 5:
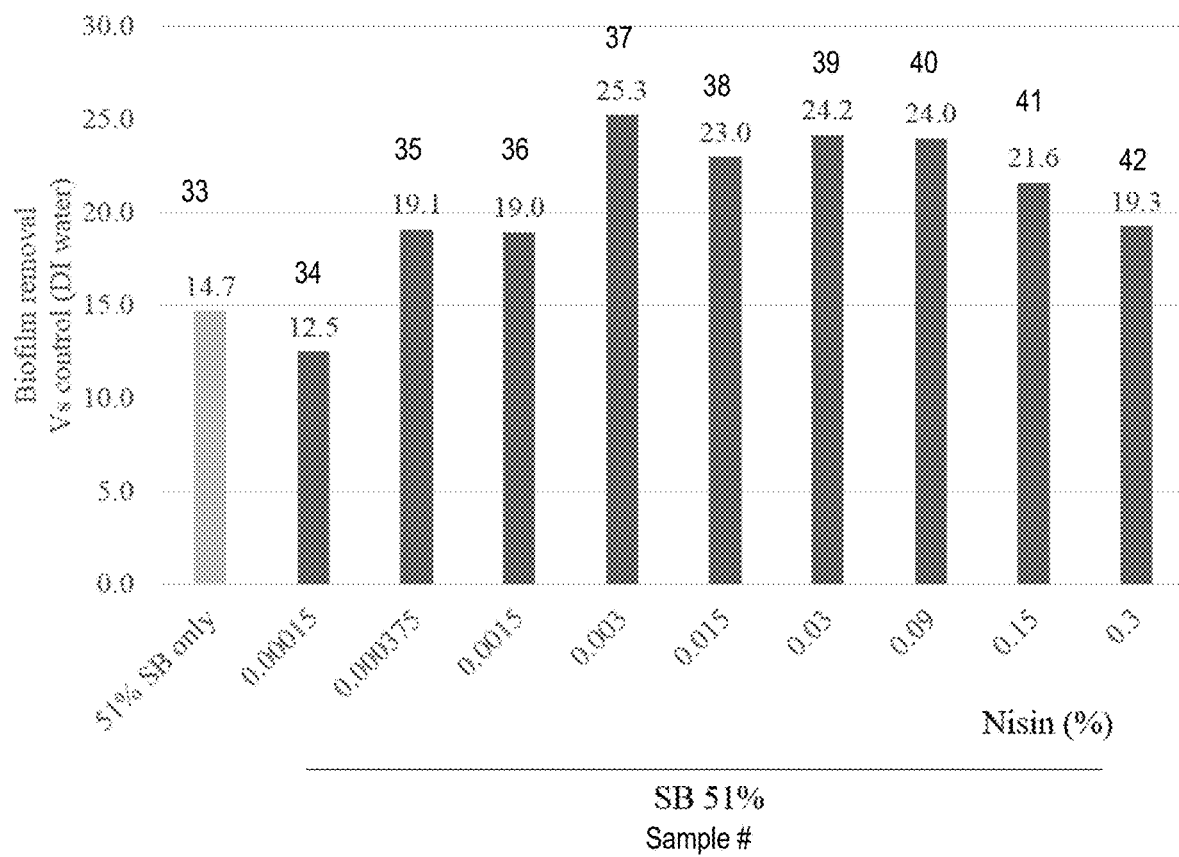
FIG. 5 graphically shows the results of Experiment 2 in which sample solution numbers 33-42 include varying concentrations of nisin and 51.0% by weight sodium bicarbonate.
Figure 6:
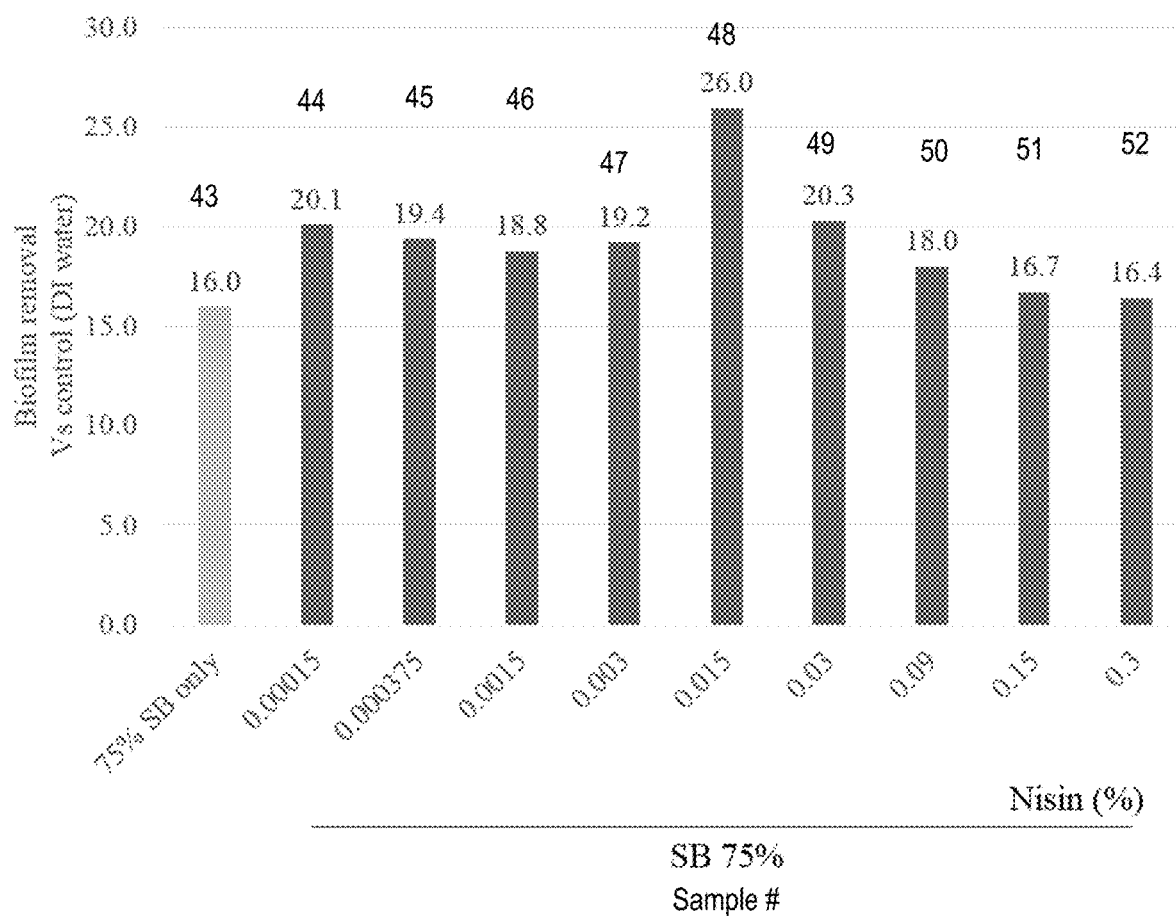
FIG. 6 graphically shows the results of Experiment 2 in which sample solution numbers 43-52 include varying concentrations of nisin and 75.0% by weight sodium bicarbonate.
Figure 7:
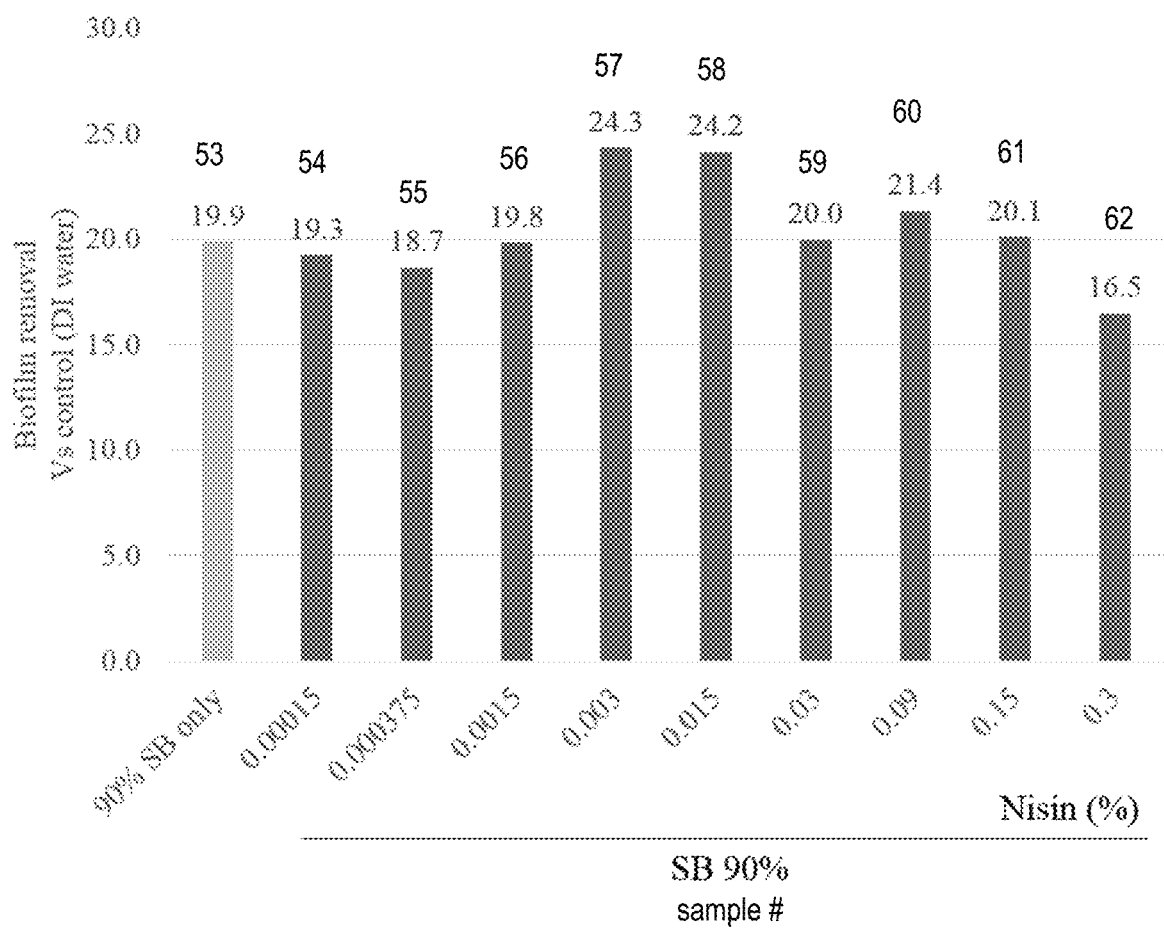
FIG. 7 graphically shows the results of Experiment 2 in which sample solution numbers 53-62 include varying concentrations of nisin and 90.0% by weight sodium bicarbonate.

It is to be understood that the invention is not limited in its application to the details set forth in the following description and the drawings.

Removing and preventing biofilm formation is the key to maintaining oral health. Biofilm can consist of multiple species of bacteria excreting a slimy glue-like substance that sticks to the surface of teeth. The most efficient measure to remove biofilm is mechanical scrubbing by a toothbrush. However, it is difficult to effectively mechanically scrub hard-to-reach areas, such as interproximal or gingival pocket spaces. One embodiment of an oral composition (e.g., a toothpaste, dentifrice, gel, mouthwash, lozenges, etc.) comprises sodium bicarbonate and nisin. Together, sodium bicarbonate and nisin remove plaque effectively. Sodium bicarbonate is widely used in oral care as anti-plaque (anti-biofilm) and anti-calculus component. Nisin has been used in oral care technology as a bactericide and has been used in food industry as a preservative for its antibacterial effect. Also, there are research reports to utilize Nisin in oral care to prevent or reduce biofilm. When used together in an oral care composition, sodium bicarbonate and nisin remove plaque more effectively than either of the two components alone.

The oral care composition may optionally include surfactants, soothing or desensitizing agents, flavoring agents, sweetening agents, humectant agents, coloring agents, additional polishing or abrasive materials, additional antimicrobial agents, binders or thickening agents, fluoride, preservatives, and water.

In one aspect, the present disclosure provides an oral care composition comprising a base formulation, sodium bicarbonate, and nisin, wherein the oral care composition removes biofilm from a tooth surface more effectively than the base formulation with the sodium bicarbonate or the nisin alone. The term "base formulation" refers to a formulation that includes at least one of the oral care ingredients described herein, but does not include sodium bicarbonate or nisin. For example, the base formulation may have the same composition as the oral care composition, except that sodium bicarbonate and nisin are absent in the base formulation. Under the same testing conditions, the oral care composition as described herein can achieve higher efficacy in removing biofilm from a tooth surface than the base formulation, the base formulation with sodium bicarbonate alone, and the base formulation with nisin alone.

Moreover, the oral care compositions discussed herein may be prepared by any suitable method.

Experiment 1

Experiment 1 treated laboratory-created biofilms with different samples of the oral care solutions as noted in Table 1.

First, a *Streptococcus mutans* ("*S mutans*") solution was cultured in a brain heart infusion ("BHI") medium overnight at 37 degrees Celsius and under anaerobic conditions. Then, the *S mutans* solution was diluted with the BHI medium with 0.5% sucrose to adjust the number of bacteria to $10^8$ cfu/ml. This step ensures that the *S mutans* concentration is consistent for each sample. Then, 200 µL of the resulting *S mutans* solution was injected into 96-well polystyrene microplates and cultured for 24 hours at 37 degrees Celsius under anaerobic conditions to form the biofilm. The biofilm in each of the wells was washed with phosphate-buffered saline ("PBS") once. Then, the biofilms in each of the wells were exposed to respective sample solutions 1-9 listed below in Table 1 for 10 minutes, and then the exposed-biofilms were each washed with PBS three times. As shown in the table below, each of the samples has different concentrations of sodium bicarbonate and nisin. Finally, the wells of exposed-biofilm were dissolved with 200 µL 1N NaOH, and the efficacy of each solution to remove the biofilm in the respective well was measured using UV-vis spectrophotometric optical density at a wavelength of 550 nm ($OD_{550}$).

TABLE 1

| | Concentration in Aqueous Solution | | |
|---|---|---|---|
| Sample # | Nisin (% by weight) | Sodium Bicarbonate (% by weight) | Biofilm Removal (%) |
| 1 | 0.000125 | 0.0 | 5.9 |
| 2 | 0.001 | 0.0 | 0.2 |
| 3 | 0.005 | 0.0 | 9.1 |
| 4 | 0.01 | 0.0 | 3.2 |
| 5 | 0 | 17.0 | 15 |
| 6 | 0.000125 | 17.0 | 28.7 |
| 7 | 0.001 | 17.0 | 23.5 |
| 8 | 0.005 | 17.0 | 25.8 |
| 9 | 0.01 | 17.0 | 19.4 |

As shown in Table 1, each of the samples has specified concentrations by weight of sodium bicarbonate and nisin. When the samples were applied to the biofilms, which a reduction of biofilm resulted. The percentage of biofilm removal represents the reduction of biofilm as a result of applying the samples to the biofilm. The results from Experiment 1 are presented in graphical form in FIG. 1, which shows that samples including both sodium bicarbonate and nisin are more effective at removing biofilm than the samples with only one of sodium bicarbonate and nisin.

Experiment 1 was carried out using an aqueous solution having the concentrations reported in Table 1. In actual oral care products using the disclosed combination, the concentrations may vary according to the specific oral care product. For example, when the oral care composition is a toothpaste, the concentrations of sodium bicarbonate and nisin reported in Table 1 may be increased because the toothpaste when used by a user will be diluted by saliva to about as much as ½ to ⅓. Alternatively, when the oral care composition is a gel or mouthwash, it may not be diluted as much during use as a toothpaste so the concentrations of sodium bicarbonate and nisin may remain closer to the concentrations reported in Table 1. Regardless of the type oral care composition, it is believed that the ratios between sodium bicarbonate and nisin will be similar to those shown in the experiment. Although the invention has been described in detail with reference to certain preferred embodiments, variations and modifications exist within the scope and spirit of the invention.

Experiment 2

Experiment 2 also treated laboratory-created biofilms with different samples of the oral care solutions as noted in Tables 2-7.

The experimental set up is the same as the experimental setup for Experiment 1, except for a few differences. First, a *Streptococcus mutans* ("*S mutans*") solution was cultured in a brain heart infusion ("BHI") medium overnight at 37 degrees Celsius and under anaerobic conditions. Then, the *S mutans* solution was diluted with the BHI medium with 0.5% sucrose to adjust the number of bacteria to $10^8$ cfu/ml. This step ensures that the *S mutans* concentration is consistent for each sample. Then, 200 µL of the resulting *S mutans* solution was injected into 96-well polystyrene microplates and cultured for 24 hours at 37 degrees Celsius under anaerobic conditions to form the biofilm. The biofilm in each of the wells was washed with deionized water ("DI") once. Then, the sample solutions were diluted to ⅓ with DI water. This step mimics the dilution of the solution by a user's saliva, when in use. Then, the biofilms in each of the wells were exposed to respective sample solutions listed below in Tables 2-7 for 10 minutes, and then the exposed-biofilms were each washed with DI water three times. As shown in the Tables 2-7 below, each of the samples 10-62 has different concentrations of sodium bicarbonate and nisin. Finally, the wells of exposed-biofilm were dissolved with 200 µL 1N NaOH, and the efficacy of each solution to remove the biofilm in the respective well was measured using UV-vis spectrophotometric optical density at a wavelength of 550 nm ($OD_{550}$).

TABLE 2

| | Concentration in Aqueous Solution | | |
|---|---|---|---|
| Sample # | Nisin (% by weight) | Sodium Bicarbonate (% by weight) | Biofilm Removal (%) |
| 10 | 0.0 | 15.0 | 7.3 |
| 11 | 0.0 | 51.0 | 14.7 |
| 12 | 0.0 | 75.0 | 16.0 |
| 13 | 0.0 | 90.0 | 19.9 |

TABLE 3

| | Concentration in Aqueous Solution | | |
|---|---|---|---|
| Sample # | Nisin (% by weight) | Sodium Bicarbonate (% by weight) | Biofilm Removal (%) |
| 14 | 0.00015 | 0.0 | 1 |
| 15 | 0.000375 | 0.0 | 0.9 |
| 16 | 0.0015 | 0.0 | −0.2 |
| 17 | 0.003 | 0.0 | −0.5 |
| 18 | 0.015 | 0.0 | −0.4 |
| 19 | 0.03 | 0.0 | 0.3 |
| 20 | 0.09 | 0.0 | −0.8 |
| 21 | 0.15 | 0.0 | −1.1 |
| 22 | 0.3 | 0.0 | −0.4 |

TABLE 4

| | Concentration in Aqueous Solution | | |
|---|---|---|---|
| Sample # | Nisin (% by weight) | Sodium Bicarbonate (% by weight) | Biofilm Removal (%) |
| 23 | 0.0 | 15.0 | 7.3 |
| 24 | 0.00015 | 15.0 | 7.7 |
| 25 | 0.000375 | 15.0 | 13.1 |
| 26 | 0.0015 | 15.0 | 17.2 |
| 27 | 0.003 | 15.0 | 19.6 |

TABLE 4-continued

| | Concentration in Aqueous Solution | | |
|---|---|---|---|
| Sample # | Nisin (% by weight) | Sodium Bicarbonate (% by weight) | Biofilm Removal (%) |
| 28 | 0.015 | 15.0 | 18.0 |
| 29 | 0.03 | 15.0 | 16.3 |
| 30 | 0.09 | 15.0 | 16.6 |
| 31 | 0.15 | 15.0 | 13.8 |
| 32 | 0.3 | 15.0 | 14.5 |

TABLE 5

| | Concentration in Aqueous Solution | | |
|---|---|---|---|
| Sample # | Nisin (% by weight) | Sodium Bicarbonate (% by weight) | Biofilm Removal (%) |
| 33 | 0.0 | 51.0 | 14.7 |
| 34 | 0.00015 | 51.0 | 12.5 |
| 35 | 0.000375 | 51.0 | 19.1 |
| 36 | 0.0015 | 51.0 | 19.0 |
| 37 | 0.003 | 51.0 | 25.3 |
| 38 | 0.015 | 51.0 | 23.0 |
| 39 | 0.03 | 51.0 | 24.2 |
| 40 | 0.09 | 51.0 | 24.0 |
| 41 | 0.15 | 51.0 | 21.6 |
| 42 | 0.3 | 51.0 | 19.3 |

TABLE 6

| | Concentration in Aqueous Solution | | |
|---|---|---|---|
| Sample # | Nisin (% by weight) | Sodium Bicarbonate (% by weight) | Biofilm Removal (%) |
| 43 | 0.0 | 75.0 | 16.0 |
| 44 | 0.00015 | 75.0 | 20.1 |
| 45 | 0.000375 | 75.0 | 19.4 |
| 46 | 0.0015 | 75.0 | 18.8 |
| 47 | 0.003 | 75.0 | 19.2 |
| 48 | 0.015 | 75.0 | 26.0 |
| 49 | 0.03 | 75.0 | 20.3 |
| 50 | 0.09 | 75.0 | 18.0 |
| 51 | 0.15 | 75.0 | 16.7 |
| 52 | 0.3 | 75.0 | 16.4 |

TABLE 7

| | Concentration in Aqueous Solution | | |
|---|---|---|---|
| Sample # | Nisin (% by weight) | Sodium Bicarbonate (% by weight) | Biofilm Removal (%) |
| 53 | 0.0 | 90.0 | 19.9 |
| 54 | 0.00015 | 90.0 | 19.3 |
| 55 | 0.000375 | 90.0 | 18.7 |
| 56 | 0.0015 | 90.0 | 19.8 |
| 57 | 0.003 | 90.0 | 24.3 |
| 58 | 0.015 | 90.0 | 24.2 |
| 59 | 0.03 | 90.0 | 20.0 |
| 60 | 0.09 | 90.0 | 21.4 |
| 61 | 0.15 | 90.0 | 20.1 |
| 62 | 0.3 | 90.0 | 16.5 |

As shown in Tables 2-7, each of the samples has specified concentrations by weight of sodium bicarbonate and nisin. When the samples were applied to the biofilms, a reduction of biofilm resulted. The percentage of biofilm removal represents the reduction of biofilm as a result of applying the samples to the biofilm. The results from Experiment 2 are presented in graphical form in FIGS. 2-7. As shown in FIGS. 4-7, the samples including both sodium bicarbonate and nisin are more effective at removing biofilm than the samples with only one of sodium bicarbonate and nisin. In particular, enhanced results may be observed when the nisin concentration ranges from 0.000375% and 0.03% by weight and the sodium bicarbonate concentration ranges from 15% to 90% by weight, when the nisin concentration ranges 0.0015% and 0.015% by weight and the sodium bicarbonate concentration ranges from 15% to 75% by weight, and when the nisin concentration ranges from 0.003% and 0.015% by weight and the sodium bicarbonate concentration ranges from 15% to 75% by weight. In one preferred embodiment, the nisin concentration may be 0.003% by weight and the sodium bicarbonate concentration may be 51% by weight.

Experiment 2 was carried out using an aqueous solution having the concentrations reported in Tables 2-7. In actual oral care products using the disclosed combination, the concentrations may vary according to the specific oral care product. Regardless of the type oral care composition, it is believed that the ratios between sodium bicarbonate and nisin will be similar to those shown in the experiment. That is, the ratio of sodium bicarbonate to nisin may range from a ratio of 500 to 1 (e.g., 15% by weight sodium bicarbonate to 0.03% by weight nisin) to a ratio of 200,000 to 1 (e.g., 75% by weight sodium bicarbonate to 0.000375% by weight nisin). More specifically, the ratio of sodium bicarbonate to nisin may range from 1000 to 1 to 25000 to 1, from 2500 to 1 to 17000 to 1, or from 3400 to 1 to 17000 to 1. In one embodiment, for example, the ratio of sodium bicarbonate to nisin may be 5000 to 1. In another embodiment, for example, the ratio of sodium bicarbonate to nisin may be 3400 to 1.

Exemplary formulations for a toothpaste are given in the tables below.

TABLE 8

| Element | Toothpaste Formulation 1 | Toothpaste Formulation 2 | Toothpaste Formulation 3 | Toothpaste Formulation 4 | Toothpaste Formulation 5 |
|---|---|---|---|---|---|
| 70% Sorbitol | 25 | 25 | 25 | 25 | 25 |
| Silica | 10 | 5 | 3 | 3 | 3 |
| Hydroxyethyl Cellulose | 0.5 | 0.5 | 0.5 | 0.5 | 0.5 |
| Xanthan Gum | 0.5 | 0.5 | 0.5 | 0.5 | 0.5 |
| Sodium Lauryl Sulfate | 0.5 | 0.5 | 0.5 | 0.5 | 0.5 |
| Titanium Oxide | 0.2 | 0.2 | 0.2 | 0.2 | 0.2 |
| Sodium Saccharin | 0.1 | 0.1 | 0.1 | 0.1 | 0.1 |
| Methyl p-hydroxy-benzoate | 1 | 1 | 1 | 1 | 1 |
| Sodium Bicarbonate | 40 | 45 | 50 | 55 | 55 |
| Nisin | 0.003 | 0.03 | 0.003 | 0.001 | 0.005 |
| Water | Balance | Balance | Balance | Balance | Balance |

TABLE 9

| Element | Toothpaste Formulation 6 | Toothpaste Formulation 7 | Toothpaste Formulation 8 | Toothpaste Formulation 9 | Toothpaste Formulation 10 |
|---|---|---|---|---|---|
| 70% Sorbitol | 10 | 10 | 10 | 10 | 10 |
| Silica | 10 | 7 | 7 | 5 | 3 |
| Crystalline cellulose | 15 | 15 | 15 | 15 | 15 |
| Lauryl Glucoside | 0.5 | 0.5 | 0.5 | 0.5 | 0.5 |
| Titanium Oxide | 0.2 | 0.2 | 0.2 | 0.2 | 0.2 |
| Sodium Saccharin | 0.1 | 0.1 | 0.1 | 0.1 | 0.1 |
| Methyl p-hydroxybenzoate | 1 | 1 | 1 | 1 | 1 |
| Sodium Bicarbonate | 40 | 45 | 50 | 55 | 60 |
| Nisin | 0.003 | 0.05 | 0.015 | 0.001 | 0.003 |
| Water | Balance | Balance | Balance | Balance | Balance |

TABLE 10

| Element | Toothpaste Formulation 11 | Toothpaste Formulation 12 | Toothpaste Formulation 13 | Toothpaste Formulation 14 | Toothpaste Formulation 15 |
|---|---|---|---|---|---|
| Glycerin | 20 | 20 | 20 | 20 | 20 |
| Calcium Carbonate | 10 | 10 | 10 | 5 | 3 |
| Hydroxyethyl Cellulose | 0.5 | 0.5 | 0.5 | 0.5 | 0.5 |
| Xanthan Gum | 0.7 | 0.7 | 0.7 | 0.7 | 0.7 |
| Cocamidopropyl betaine | 0.5 | 0.5 | 0.5 | 0.5 | 0.5 |
| Sodium Saccharin | 0.1 | 0.1 | 0.1 | 0.1 | 0.1 |
| Methyl p-hydroxybenzoate | 1 | 1 | 1 | 1 | 1 |
| Sodium Bicarbonate | 40 | 40 | 45 | 55 | 70 |
| Nisin | 0.001 | 0.05 | 0.002 | 0.002 | 0.003 |
| Water | Balance | Balance | Balance | Balance | Balance |

TABLE 11

| Element | Toothpaste Formulation 16 | Toothpaste Formulation 17 | Toothpaste Formulation 18 | Toothpaste Formulation 19 | Toothpaste Formulation 20 |
|---|---|---|---|---|---|
| Glycerin | 20 | 20 | 20 | 20 | 20 |
| Silica | 30 | 10 | 5 | 5 | 5 |
| Xanthan Gum | 0.5 | 0.5 | 0.5 | 0.5 | 0.5 |
| PEG-60 hydrogenated castor oil | 1 | 1 | 1 | 1 | 1 |
| Alkyl Glycoside (C8~16) | 1 | 1 | 1 | 1 | 1 |
| Titanium Oxide | 0.2 | 0.2 | 0.2 | 0.2 | 0.2 |
| Sodium Saccharin | 0.1 | 0.1 | 0.1 | 0.1 | 0.1 |
| Methyl p-hydroxybenzoate | 1 | 1 | 1 | 1 | 1 |
| Sodium Bicarbonate | 30 | 45 | 55 | 60 | 60 |
| Nisin | 0.003 | 0.003 | 0.03 | 0.001 | 0.05 |
| Water | Balance | Balance | Balance | Balance | Balance |

TABLE 12

| Element | Toothpaste Formulation 21 | Toothpaste Formulation 22 | Toothpaste Formulation 23 | Toothpaste Formulation 24 |
|---|---|---|---|---|
| Glycerin | 20 | 18 | 15 | 15 |
| Calcium Carbonate | 15 | 10 | 5 | 3 |
| Xanthan Gum | 0.9 | 0.9 | 0.9 | 0.9 |
| Cocamidopropyl betaine | 1 | 1 | 1 | 1 |
| Sodium Saccharin | 0.1 | 0.1 | 0.1 | 0.1 |
| Methyl p-hydroxybenzoate | 1 | 1 | 1 | 1 |
| Sodium Bicarbonate | 40 | 45 | 55 | 60 |
| Nisin | 0.01 | 0.04 | 0.04 | 0.01 |
| Water | Balance | Balance | Balance | Balance |

Exemplary formulations for a gel are given in the tables below.

TABLE 13

| Element | Gel Formulation 1 | Gel Formulation 2 | Gel Formulation 3 | Gel Formulation 4 |
|---|---|---|---|---|
| Hydroxypropylmethyl Cellulose | 0.3 | 0.3 | 0.3 | 0.3 |
| Glycerin | 10 | 10 | 10 | 10 |
| Sorbitol | 5 | 5 | 5 | 5 |
| Propylene glycol | 4 | 4 | 4 | 4 |
| Sodium Bicarbonate | 45 | 45 | 50 | 55 |
| Nisin | 0.003 | 0.03 | 0.001 | 0.02 |
| Flavor | 0.1 | 0.1 | 0.1 | 0.1 |
| Water | Balance | Balance | Balance | Balance |

TABLE 14

| Element | Gel Formulation 5 | Gel Formulation 6 | Gel Formulation 7 | Gel Formulation 8 |
|---|---|---|---|---|
| Xanthan Gum | 1.5 | 1.5 | 1.5 | 1.5 |
| Glycerin | 25 | 25 | 25 | 25 |
| Propylene glycol | 2 | 2 | 2 | 2 |
| Sodium Bicarbonate | 45 | 50 | 55 | 55 |
| Nisin | 0.005 | 0.05 | 0.0001 | 0.003 |
| Flavor | 0.1 | 0.1 | 0.1 | 0.1 |
| Water | Balance | Balance | Balance | Balance |

TABLE 15

| Element | Gel Formulation 9 | Gel Formulation 10 | Gel Formulation 11 | Gel Formulation 12 |
| --- | --- | --- | --- | --- |
| Agar | 0.2 | 0.2 | 0.2 | 0.2 |
| Gelatin | 1.5 | 1.5 | 1.5 | 1.5 |
| Glycerin | 10 | 10 | 10 | 10 |
| Propylene Glycol | 2 | 2 | 2 | 2 |
| Sodium Saccharin | 0.01 | 0.01 | 0.01 | 0.01 |
| Sodium Bicarbonate | 40 | 40 | 60 | 60 |
| Nisin | 0.003 | 0.04 | 0.003 | 0.04 |
| Flavor | 0.1 | 0.1 | 0.1 | 0.1 |
| Water | Balance | Balance | Balance | Balance |

Exemplary formulations for an oral tablet for a denture cleanser are given in the tables below.

TABLE 16

| Element | Tablet Formulation 1 | Tablet Formulation 2 |
| --- | --- | --- |
| Sodium Carbonate | 20 | 20 |
| Sodium Perborate | 10 | 10 |
| Anhydrous Citric Acid | 7 | 7 |
| Sodium Lauryl Sulfate | 5 | 5 |
| Sodium Edetate | 1 | 1 |
| Sodium Bicarbonate | 45 | 50 |
| Nisin | 0.002 | 0.001 |
| Magnesium Stearate | 11.998 | 6.999 |

Exemplary formulations for a chewable oral cleansing tablet are given in the tables below.

TABLE 17

| Element | Tablet Formulation 3 | Tablet Formulation 4 |
| --- | --- | --- |
| Xylitol | 40 | 40 |
| Aspartame | 0.01 | 0.01 |
| Sodium Bicarbonate | 45 | 50 |
| Nisin | 0.001 | 0.005 |
| Magnesium Stearate | 14.989 | 9.985 |

TABLE 18

| Element | Tablet Formulation 5 | Tablet Formulation 6 |
| --- | --- | --- |
| Anhydrous Citric Acid | 10 | 10 |
| Sodium Lauryl Sulfoacetate | 1 | 1 |
| Sodium Bicarbonate | 50 | 55 |
| Nisin | 0.005 | 0.01 |
| Sorbitol | 38.995 | 33.99 |

Exemplary formulations for an effervescent tablet for gargling are given in the table below.

| Element | Tablet Formulation 7 | Tablet Formulation 8 |
| --- | --- | --- |
| Anhydrous Sodium Sulfate | 13 | 13 |
| Dibasic Sodium Phosphate | 10 | 10 |
| Polyethylene Glycol | 3 | 3 |
| Sodium Monofluorophosphate | 0.1 | 0.1 |
| Sodium Bicarbonate | 50 | 55 |
| Nisin | 0.01 | 0.004 |
| Sorbitol | 23.89 | 18.896 |

Exemplary formulations for a chewing gum are given in the tables below.

TABLE 19

| Element | Chewing Gum Formulation 1 | Chewing Gum Formulation 2 | Chewing Gum Formulation 3 |
| --- | --- | --- | --- |
| Gum base | 20 | 20 | 20 |
| Reduced Palatinose | 28 | 23 | 23 |
| Sodium Bicarbonate | 45 | 55 | 55 |
| Nisin | 0.004 | 0.002 | 0.03 |
| Xylitol | 6.896 | 1.898 | 1.87 |
| Flavor | 0.1 | 0.1 | 0.1 |

TABLE 20

| Element | Chewing Gum Formulation 4 | Chewing Gum Formulation 5 | Chewing Gum Formulation 6 |
| --- | --- | --- | --- |
| Gum base | 25 | 25 | 20 |
| Erythritol | 10 | 10 | 10 |
| Sodium Bicarbonate | 45 | 45 | 55 |
| Nisin | 0.001 | 0.02 | 0.005 |
| Maltitol | 12 | 12 | 12 |
| Xylitol | 7.899 | 7.88 | 2.895 |
| Flavor | 0.1 | 0.1 | 0.1 |

Although the invention has been described in detail with reference to certain preferred embodiments, variations and modifications exist within the scope and spirit of the invention.

What is claimed is:

1. An oral care composition that aids in cleaning teeth, the oral care composition comprising:
    between 15% by weight and 75% by weight sodium bicarbonate and between 0.000375% by weight and 0.09% by weight of nisin, wherein a ratio of sodium bicarbonate to nisin is at least 500 to 1 and does not exceed 200,000 to 1.

2. The oral care composition of claim 1, wherein the composition comprises between 51% and 75% by weight of sodium bicarbonate and between 0.000375% and 0.03% by weight of nisin.

3. The oral care composition of claim 1, wherein the composition comprises between 15% and 51% by weight of sodium bicarbonate and between 0.000375% and 0.03% by weight of nisin.

4. The oral care composition of claim 1, the composition comprises between 0.000375% and 0.03% by weight of nisin.

5. The oral care composition of claim 1, wherein the composition comprises between 0.0015% and 0.015% by weight of nisin.

6. The oral care composition of claim 1, wherein the composition comprises between 0.003% and 0.015% by weight of nisin.

7. The oral care composition of claim 1, wherein the nisin concentration is 0.003% by weight and the sodium bicarbonate concentration is 51% by weight.

8. The oral care composition of claim 1, wherein the oral care composition includes one or more of surfactants, soothing agents, desensitizing agents, flavoring agents, sweetening agents, humectant agents, coloring agents, polishing material, abrasive materials, antimicrobial agents, binders, thickening agents, fluoride, preservatives, and water.

9. A method of treating teeth comprising: applying an oral care composition to a tooth surface, the composition includes between 15% by weight and 75% by weight sodium bicarbonate and between 0.000375% by weight and 0.09% by weight of nisin, wherein a ratio of sodium bicarbonate to nisin is at least 500 to 1 and does not exceed 200,000 to 1.

10. The method of claim 9, wherein the composition comprises between 15% and 75% by weight of sodium bicarbonate and between 0.000375% and 0.05% by weight of nisin.

11. The method of claim 9, wherein the composition comprises between 0.000375% and 0.03% by weight of nisin.

12. An oral care composition comprising a base formulation, sodium bicarbonate, and nisin, wherein the oral care composition removes biofilm from a tooth surface more effectively than the base formulation with the sodium bicarbonate or the nisin alone, wherein the oral care compositions includes between 15% by weight and 75% by weight sodium bicarbonate and between 0.000375% by weight and 0.05% by weight of nisin, wherein the ratio of sodium bicarbonate to nisin is at least 500 to 1 and wherein the ratio of sodium bicarbonate to nisin does not exceed 200,000 to 1.

13. The oral care composition of claim 12, wherein the ratio of sodium bicarbonate to nisin ranges from 1000 to 1 to 25000 to 1.

14. The oral care composition of claim 12, wherein the ratio of sodium bicarbonate to nisin ranges from 2500 to 1 to 17000 to 1.

15. The oral care composition of claim 12, wherein the ratio of sodium bicarbonate to nisin ranges from 3400 to 1 to 17000 to 1.

16. The oral care composition of claim 12, wherein the ratio of sodium bicarbonate to nisin is 3400 to 1.

17. The oral care composition of claim 12, wherein the oral care composition includes one or more of surfactants, soothing agents, desensitizing agents, flavoring agents, sweetening agents, humectant agents, coloring agents, polishing material, abrasive materials, antimicrobial agents, binders, thickening agents, fluoride, preservatives, and water.

* * * * *